US00PP37581P2

(12) United States Plant Patent
Boxriker

(10) Patent No.: US PP37,581 P2
(45) Date of Patent: Aug. 11, 2026

(54) ***DAHLIA* PLANT NAMED 'KLEDH24740'**

(50) Latin Name: ***Dahlia* sp.**
Varietal Denomination: KLEDH24740

(71) Applicant: KLEMM + SOHN GMBH & CO. KG, Stuttgart (DE)

(72) Inventor: Maike Boxriker, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/335,244

(22) Filed: Sep. 22, 2025

(51) Int. Cl.
*A01H 5/02* (2018.01)
*A01H 6/14* (2018.01)

(52) U.S. Cl.
USPC ..... Plt./321

(58) Field of Classification Search
USPC ..... Plt./321
See application file for complete search history.

(56) References Cited

PUBLICATIONS https://josvainiugeles.It/wp-content/uploads/2024/09/Selecta-Annuals-2025.pdf (Retrieved from the Internet on Dec. 9, 2025).*

* cited by examiner

*Primary Examiner* — Susan McCormick Ewoldt
(74) *Attorney, Agent, or Firm* — Weatherly IP Solutions, LLC; John E. Pritchard; James M. Weatherly

(57) ABSTRACT

A new *Dahlia* plant designated 'KLEDH24740' particularly distinguished by flowers with yellow to white petals at the marginal zone and at the basal quarter and a semi-spreading plant habit, is disclosed.

1 Drawing Sheet

Genus and species: *Dahlia* sp.
Variety denomination: 'KLEDH24740'.

BACKGROUND

The present invention comprises a new and distinct variety of *Dahlia,* botanically known as *Dahlia* sp., and hereinafter referred to by the variety name 'KLEDH24740'. 'KLEDH24740' originated from an open pollination in a field with the female parent 'DH-2018-5130' (unpatented) and an unknown male *Dahlia* plant in the summer of 2020 in Latina, Italy. In March 2021 a seedling was selected and named 'KLEDH24740'. 'KLEDH24740' was first vegetatively propagated by vegetative cuttings in April 2021 in Latina, Italy. 'KLEDH24740' was found to reproduce true to type in successive generations of asexual propagation.

SUMMARY

The following are the most outstanding and distinguishing characteristics of 'KLEDH24740' when grown using standard horticultural practices in Latina, Italy.

1. Flowers with yellow to white petals at the marginal zone and at the basal quarter; and
2. Semi-spreading plant habit.

DESCRIPTION OF THE PHOTOGRAPH

This new *Dahlia* plant is illustrated by the accompanying photograph taken in May 2024 of a fourteen weeks old plant grown in a greenhouse in Stuttgart, Germany.

The photograph shows the whole plant, including the foliage, buds, and inflorescences and the colors shown are as true as can be reasonably obtained by conventional photographic procedures.

DESCRIPTION OF 'KLEDH24740'

The following detailed descriptions set forth the distinctive characteristics of 'KLEDH24740'. The data which define these characteristics were collected from asexual reproductions carried out in Latina, Italy. Data was collected on 16-week-old plants, with one pinch and grown under natural light in a greenhouse. Color references are to The R.H.S. Colour Chart of The Royal Horticultural Society of London (R.H.S.), 5$^{th}$ edition (2007).

Classification:
- *Family*.—Asteraceae.
- *Botanical*.—*Dahlia* sp.
- *Designation*.—'KLEDH24740'.

Parentage:
- *Female parent*.—'DH-2018-5130' (unpatented).
- *Male parent*.—Unknown.

Propagation:
- *Type*.—Vegetative terminal cuttings.
- *Time to produce a rooted young plant*.—3 to 4 weeks.
- *Time to produce a flowering plant*.—About 10 weeks.
- *Root description*.—Fine, white, color N155C.
- *Rooting habit*.—Freely branching and moderately dense.

Plant description:
- *Plant and growth habit*.—Semi-spreading.
- *Plant height*.—To the top of foliar plane: About 20 cm. Including inflorescence: About 27 cm.
- *Plant diameter*.—About 34 cm.

Lateral branches:
- *Length*.—Up to the last pair of leaves: About 16 cm. Including inflorescence: About 26 cm.
- *Diameter*.—About 0.4 cm.
- *Internode length*.—From 3 cm to 6 cm.
- *Strength*.—Medium strong.
- *Texture*.—Smooth.
- *Color*.—Close to 79A at the front and 138A at the back.

Foliage description:
- *Arrangement*.—Opposite, simple at the middle third of the stem, pinnate at the base.

*Length*.—About 12.5 cm.
*Width*.—About 5.5 cm.
*Shape*.—Ovate.
*Apex*.—Broadly acuminate.
*Base*.—Acute.
*Margin*.—Serrate.
*Venation pattern*.—Pinnate.
*Venation color*.—144A.
*Texture*.—Upper and lower surface: Little hairy on the edges, slightly rugose and glossy.
*Color*.—Immature: Upper surface: N137B. Lower surface: 191B. Mature: Upper surface: 137B. Lower surface: close to 138B.

Petioles:
*Length*.—About 3.5 cm.
*Diameter*.—0.3 cm in the mid-section, 0.4 cm at the node.
*Texture*.—Upper surface: Smooth. Lower surface: Smooth.
*Color*.—Upper surface: N77A. Lower surface: Close to 148A.

Inflorescence description:
*Appearance and arrangement*.—Composite head inflorescence, daisy eyed, held above the foliage.
*Fragrance*.—None detected.
*Time to flower*.—About 10 weeks after potting.
*Post-production longevity*.—Plants flower continuously from spring through autumn.

Inflorescence bud:
*Height*.—About 1.5 cm.
*Diameter*.—About 2 cm.
*Shape*.—Globular.
*Color*.—143A at the base with 153C toward the tips.

Inflorescence size:
*Diameter*.—About 7 cm.
*Depth* (*height*).—About 4.5 cm.
*Disc diameter*.—Not visible (about 1 cm at anther extrusion).
*Receptacle height*.—0.5 cm.
*Receptacle diameter*.—2.5 cm.
*Receptacle color*.—144A.

Ray florets:
*Quantity per inflorescence*.—115 in about 8 whorls.
*Length*.—3.3 cm.
*Width*.—1.6 cm.
*Shape*.—Obovate.
*Apex*.—Slightly Pointed.
*Base*.—Fused in a tube.
*Margin*.—Entire.
*Aspect*.—Keeled.
*Texture*.—Upper surface: Smooth. Lower surface: Smooth.
*Color*.—Immature: Upper surface: Main color NN155D, secondary color 1A. Lower surface: Main color NN155D, secondary color 1A. Mature: Upper surface: Outermost florets 1A, all other petals main color NN155D, secondary color 1A at marginal zone and at basal quarter. Lower surface: Outermost petals 1B, all other petals main color NN155D, secondary color 1B at marginal zone and at basal quarter.

Disc florets:
*Quantity per inflorescence*.—50.
*Length*.—About 1.3 cm.
*Diameter*.—About 0.3 cm.
*Shape*.—Tubular.
*Texture*.—Inner surface: Smooth. Outer surface: Smooth.
*Color*.—Immature: Inner surface: 1D. Outer surface: 1D. Mature: Inner surface: 4D. Outer surface: 4D.

Phyllaries:
*Quantity per inflorescence*.—5 at the external whorl, 12 in the internal whorls.
*Length*.—External phyllaries about 1.4 cm; inner phyllaries about 2 cm.
*Width*.—About 0.5 cm.
*Shape*.—Lanceolate to spatulate.
*Apex*.—Acute.
*Base*.—External phyllaries attenuate; internal whorls fused.
*Margin*.—Entire.
*Texture*.—Upper surface: Smooth and slightly glossy. Lower surface: Smooth and slightly glossy.
*Color*.—Upper surface: external whorl: 137A. internal whorl: 144A at the base to 145B at the tips. Lower surface: external whorl: 138A. internal whorl: 144A at the base to 145C at the tips.

Peduncles:
*Length, terminal peduncle*.—About 10 cm.
*Length, axillary peduncle*.—About 4.5 cm.
*Diameter*.—About 0.3 cm.
*Aspect*.—Semi-upright.
*Strength*.—Strong.
*Texture*.—Smooth.
*Color*.—146C to 187A.

Reproductive organs:
*Androecium*.—Only on disc florets. Quantity per floret: 5 stamens with fused anthers. Filament length: 0.4 cm. Filament color: 155B. Anther shape: Oblong. Anther length: 0.3 cm. Anther color: 21A. Pollen amount: Moderate. Pollen color: 21A.
*Gynoecium*.—Quantity per floret: 1. Pistil length: About 1.5 cm. Style length: 0.9 cm. Style color: 160D. Stigma shape: Bipartite. Stigma color: 23A. Ovary color: 145D.

Fruit and seed set: Not observed.

Disease and pest/insect resistance: No disease resistance observed.

COMPARISON OF 'KLEDH24740' WITH PARENTAL LINE AND KNOWN VARIETY

'KLEDH24740' is distinguished from the female parent as described in Table 1.

TABLE 1

Comparison with Parental Line

| Trait | Variety 'KLEDH24740' | Female parent 'DH-2018-5130' |
|---|---|---|
| Flower color | Yellow to white at marginal zone and at basal quarter | Purple pink |

'KLEDH24740' can be compared to the commercial *Dahlia* variety 'KLEDH17008' (U.S. plant Pat. No. 31,053). Differences between the varieties are described in Table 2.

TABLE 2

Comparison with Similar Variety

| Trait | Variety 'KLEDH24740' | Commercial line 'KLEDH17008' (U.S. Plant Pat. No. 31,053) |
|---|---|---|
| Flower color | Yellow to white at marginal zone and at basal quarter | Solid yellow |

I claim:

1. A new and distinct variety of *Dahlia* Plant Named 'KLEDH24740', as illustrated and described herein.

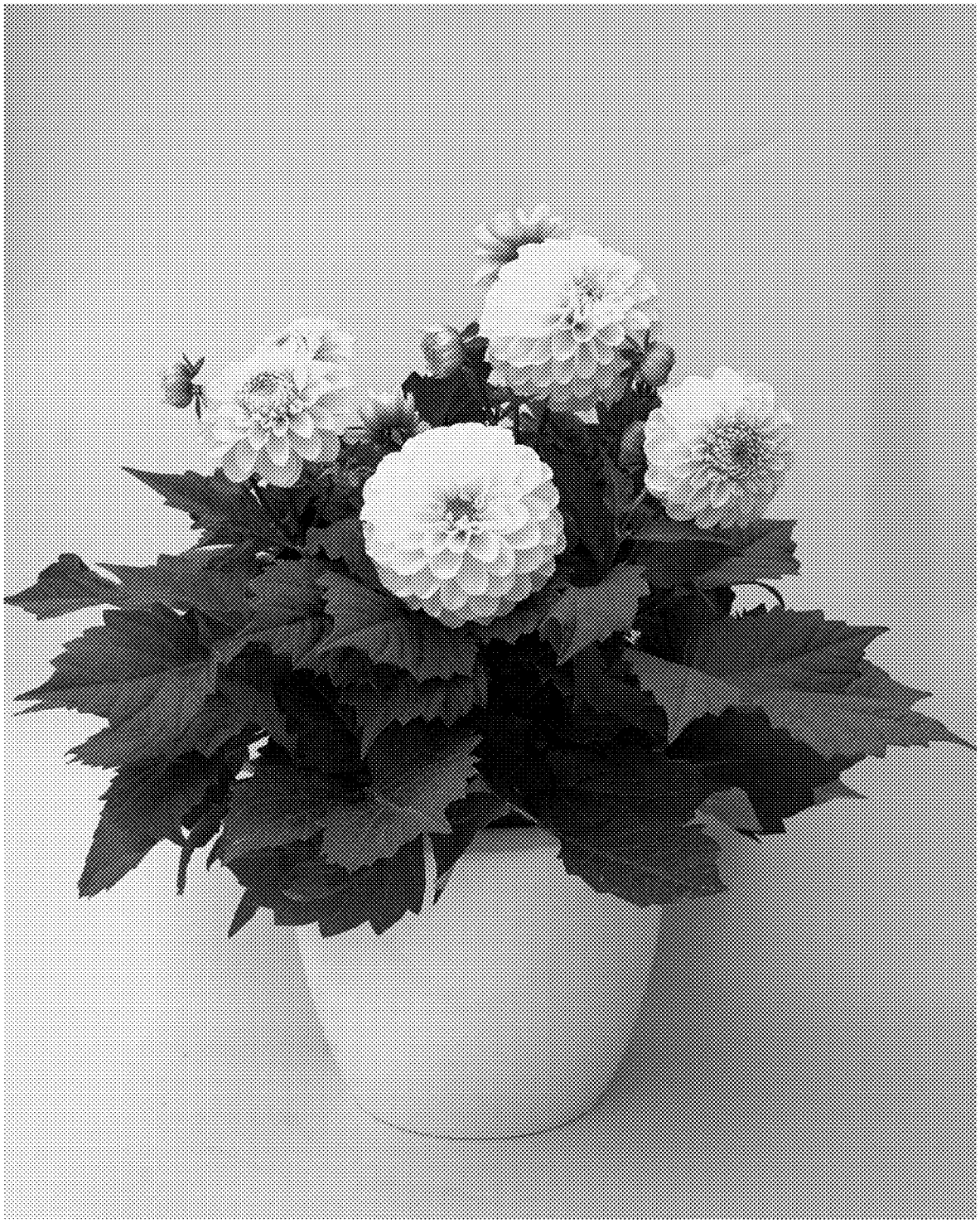

* * * * *